(12) United States Patent
Alimi et al.

(10) Patent No.: US 7,924,028 B2
(45) Date of Patent: Apr. 12, 2011

(54) METHOD AND SYSTEM FOR ADJUSTING CHARACTERISTICS OF INTEGRATED RELATIVE HUMIDITY SENSOR

(75) Inventors: Yousef Alimi, Allen, TX (US); Richard Alan Davis, Plano, TX (US)

(73) Assignee: Honeywell International Inc., Morristown, NJ (US)

( * ) Notice: Subject to any disclaimer, the term of this patent is extended or adjusted under 35 U.S.C. 154(b) by 227 days.

(21) Appl. No.: 12/052,535

(22) Filed: Mar. 20, 2008

(65) Prior Publication Data

US 2009/0237090 A1    Sep. 24, 2009

(51) Int. Cl.
  *G01R 27/26*  (2006.01)
(52) U.S. Cl. ........................ 324/664; 324/689
(58) Field of Classification Search .................. 324/658, 324/664, 678, 686, 698
See application file for complete search history.

(56) References Cited

U.S. PATENT DOCUMENTS

| | | | |
|---|---|---|---|
| 4,831,325 A | * | 5/1989 | Watson, Jr. ................... 324/678 |
| 6,230,543 B1 | | 5/2001 | Froehling et al. |
| 6,724,612 B2 | | 4/2004 | Davis et al. |
| 6,867,602 B2 | | 3/2005 | Davis et al. ................... 324/664 |

OTHER PUBLICATIONS

Written Opinion and International Search Report from corresponding PCT Application Serial No. PCT/US2009/034824, mailed Jun. 29, 2009, 7 pages.

* cited by examiner

*Primary Examiner* — Vincent Q Nguyen
(74) *Attorney, Agent, or Firm* — Shumaker & Sieffert, P.A.

(57) ABSTRACT

A method and system for adjusting characteristics of a relative humidity sensor in order to achieve a desired value of accuracy is presented. A relative humidity sensor charge balance circuit includes a series of sensing capacitors $Cx1$, $Cx2$ including a thin porous platinum top plate, a humidity sensitive polyimide dielectric, and two metal bottom plates on a semiconductor substrate; and two fixed oxide capacitances Cref, and C0. Changes in humidity affect the humidity sensitive dielectric thereby causing changes in the sensing capacitive value of the capacitive circuit. The charge in the sensing capacitor and the fixed capacitor C0 can be controlled separately by adjusting and/or trimming the supply voltage using a voltage trimmer; thereby the slope and offset of the relative humidity sensor circuit can be modified and controlled to particular desired values.

7 Claims, 6 Drawing Sheets

US 7,924,028 B2

METHOD AND SYSTEM FOR ADJUSTING CHARACTERISTICS OF INTEGRATED RELATIVE HUMIDITY SENSOR

TECHNICAL FIELD

Embodiments are related to semiconductor wafer-based devices. Embodiments are also related to relative humidity sensors. Embodiments are additionally related to methods and systems for adjusting characteristics of relative humidity sensors.

BACKGROUND OF THE INVENTION

Humidity plays a very major role in various industrial and commercial applications. Monitoring and controlling humidity is of great importance for the reliable operation of various systems. For example, solid-state semiconductor devices are found in most electronic components today. Semiconductor-based sensors are fabricated utilizing semiconductor processes. Humidity sensors represent but one class of semiconductor-based sensors finding a useful industrial application. Modern manufacturing processes, for example, generally require measurement of moisture contents corresponding to dew points between −40° C. and 180° C., or a relative humidity between 1% and 100%. There is also a need for a durable, compact, efficient moisture detector that can be used effectively in these processes to measure very small moisture content in gaseous atmospheres.

Humidity can be measured by a number of techniques. In a semiconductor-based system, for example, humidity can be measured based upon the reversible water absorption characteristics of polymeric materials. The absorption of water into a sensor structure causes a number of physical changes in the active polymer. These physical changes can be transduced into electrical signals which are related to the water concentration in the polymer and which in turn are related to the relative humidity in the air surrounding the polymer. Two of the most common physical changes are variations in resistance and the change in dielectric constant, which can be respectively translated into a resistance change and a capacitance change. It has been found, however, that elements utilized as resistive components suffer from the disadvantage that there is an inherent dissipation effect caused by the dissipation of heat due to the current flow in the elements necessary to make a resistance measurement. The result includes erroneous readings, among other problems.

Elements constructed to approximate a pure capacitance avoid the disadvantages of the resistive elements. It is important in the construction of capacitive elements, however, to avoid problems that can arise with certain constructions for such elements. In addition, there can also be inaccuracy incurred at high relative humidity values where high water content causes problems due to excessive stress and the resulting mechanical shifts in the components of the element. By making the component parts of the element thin, it has been found that the above-mentioned problems can be avoided and the capacitance type element can provide a fast, precise measurement of the relative humidity content over an extreme range of humidity as well as over an extreme range of temperature and pressure and other environmental variables.

A conventional capacitive humidity sensor, in general, can include a semiconductor substrate, and a pair of electrodes, which are formed on a surface of the semiconductor substrate and face each other across a particular distance. A humidity-sensitive film may also be placed between the electrodes and formed on a surface of the semiconductor substrate. The capacitance of the film changes in response to humidity. The sensor detects humidity by detecting changes in capacitance between the pair of electrodes in response to variations in the surrounding humidity. Humidity sensing elements of the capacitance sensing type usually include a moisture-insensitive, non-conducting structure with appropriate electrode elements mounted or deposited on the structure, along with a layer or coating of a dielectric, highly moisture-sensitive material overlaying the electrodes and positioned so as to be capable of absorbing water from the surrounding atmosphere and attaining equilibrium in a short period of time. The response offset and slope for the integrated relative humidity sensor can be set to particular values in order to achieve a desired value of accuracy for the sensor.

FIG. 1 illustrates a "prior art" charge balancing circuit 100 of a humidity sensor for transforming measurements of relative humidity into a linear voltage. The high impedance capacitive nature of the humidity sensor can be readily handled by control of charge. FIG. 1 includes fixed capacitors C0, C1, C2, C3, and Cref that are designed to be insensitive to humidity and that can be fabricated at the same time and from the same materials. A humidity sensitive capacitor Cx can be designed to be sensitive to humidity and is fabricated at a different time and from different materials than the aforementioned capacitors. A switching matrix 120 varies the wiring scheme for capacitors: Cx, C0, and Cref utilizing two-phase, non-overlapping, dual polarity clocks, as can be provided by clock generator 110. Inverters A1, A2, and A3, and capacitor C1, and a pair of associated transmission gates 130 and 140 form a high gain comparator. The capacitor C2 and its pair of associated transmission gates 150 and 160 are the switched capacitor equivalent of a resistor which can be coupled with amplifier A4 and feedback capacitor C3 from an integrator. The capacitive values of the sensing capacitor Cx and the fixed capacitor C0 can be varied by laser trimming or by etching the sensing capacitor Cx to create voids in order to keep their values substantially equal.

FIGS. 2A and 2B illustrate "prior art" charge balancing circuit 200 and 250 during "Phase 1" and "Phase 2" operation respectively. In Phase 1 C0 is pulled up to Vcc and Cx is pulled down to GND and vice versa during Phase 2. Thus a periodic differential voltage can be created which is a function of the difference in capacitance values. The following equations mathematically describe the operation of the circuit 200 and 250. The charge at the summing node during Phase 1 and 2, can be calculated utilizing equations (1) and (2) respectively. The negative feedback results in Qs1 and Vs1 being substantially equal to Qs2 and Vs2. equation (3) mathematically describes the resulting transfer function for the complete circuit operation.

$$Qs1 = Cx^*Vs1 + C0^*(Vs1-Vcc) + Cref^*(Vs1-Vout) \quad (1)$$

$$Qs2 = Cx^*(Vs2-Vcc) + C0^*Vs2 + Cref^*Vs2 \quad (2)$$

$$Vout = Vcc^*(Cx^*(1+\alpha^*RH)/Cref) - Vcc^*(C0/Cref) \quad (3)$$

In a majority of prior art humidity sensors the humidity sensitive capacitor Cx can be laser trimmed for offset adjustment and a photo mask layer of the reference capacitor C0 can be varied for slope adjustment. The laser trimming of humidity sensitive capacitor Cx for offset adjustment can introduce a reliability issue, due to exposure of the trimming site of the humidity sensitive capacitor to various application conditions. Also, the slope adjustment by variation of photo mask layer is costly and time consuming.

Based on the foregoing it is believed that a need exists for an improved methods and systems for adjusting characteristics of the relative humidity sensors in order to provide a more accurate measurement of humidity as will be disclosed in further detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for improved sensor methods and systems.

It is another aspect of the present invention to provide for an improved method and system for capacitive balancing of relative humidity sensors.

It is another aspect of the present invention to provide for an improved method and system for adjusting characteristics of relative humidity sensors.

The aforementioned aspects and other objectives and advantages can now be achieved as described herein. A method and system for adjusting the characteristics of a relative humidity sensor in order to achieve a desired value of accuracy is disclosed. The sensor includes a pair of electrodes with a gap-interposed therebetween to form a sensing capacitor on a silicon substrate with a silicon oxide film formed on a surface thereof. The charge in the sensing capacitor and a fixed capacitor can be controlled separately by adjusting and/or trimming a supply voltage utilizing a voltage trimmer to achieve capacitive balance in a charge balance circuit. The slope and offset of the relative humidity sensor can also be modified and controlled to particular desired values by adjusting the voltage for the sensing capacitor and the fixed capacitor respectively.

The pair of electrodes can be connected to a signal processing circuit for detecting the variation of the electrostatic capacitance between the pair of electrodes.

The relative humidity sensor can be formed on the semiconductor substrate, and thus the signal processing circuit for detecting the variation of the capacitance type humidity sensor can be formed on the principal surface of the semiconductor substrate.

The capacitance formed between the pair of electrodes changes in accordance with ambient humidity.

The capacitive values of the sensing capacitor and the fixed capacitor can be adjusted while keeping their values substantially equal. The ability of adjusting the charge level of the sensing capacitor Cx and the fixed capacitor C0 disclosed herein can therefore provide for better control of sensor output accuracy and thereby enhance the reliability of the sensor.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
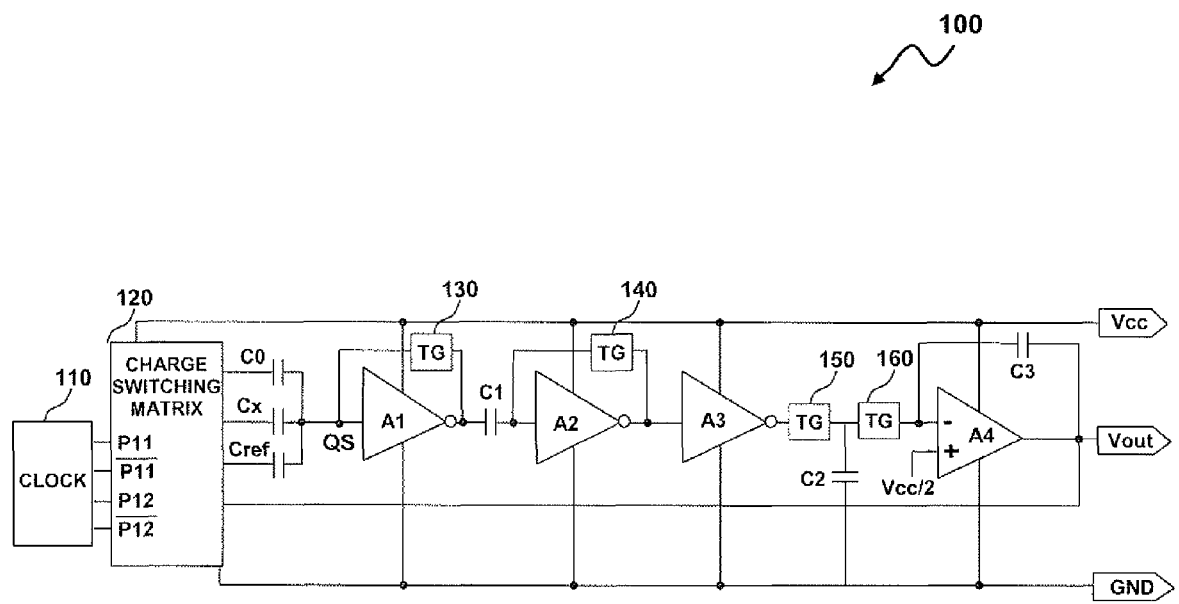
FIG. 1 illustrates a "prior art" charge balancing circuit for transducing relative humidity to a linear voltage.
Figure 2A:
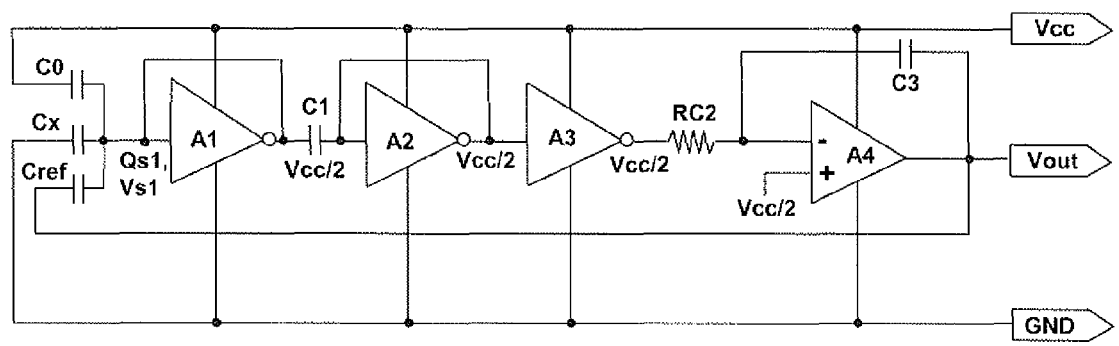
FIG. 2A illustrates the "prior art" charge balancing circuit during Phase 1 operation.
Figure 2B:
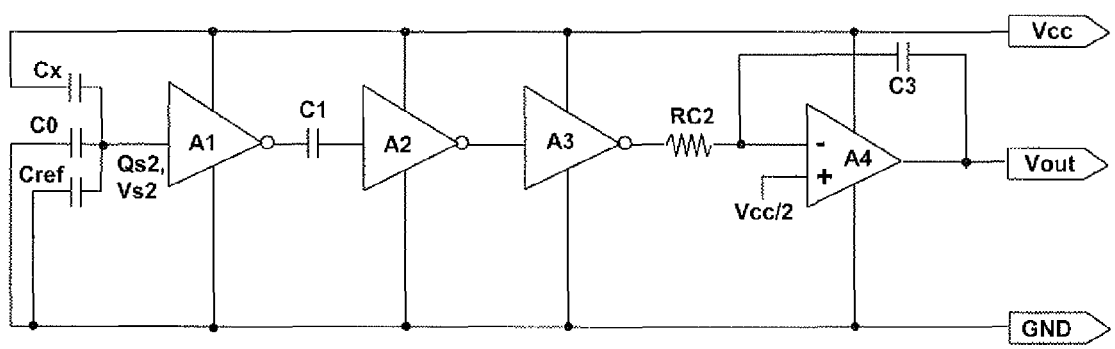
FIG. 2B illustrates the "prior art" charge balancing circuit during Phase 2 operation.
Figure 3:
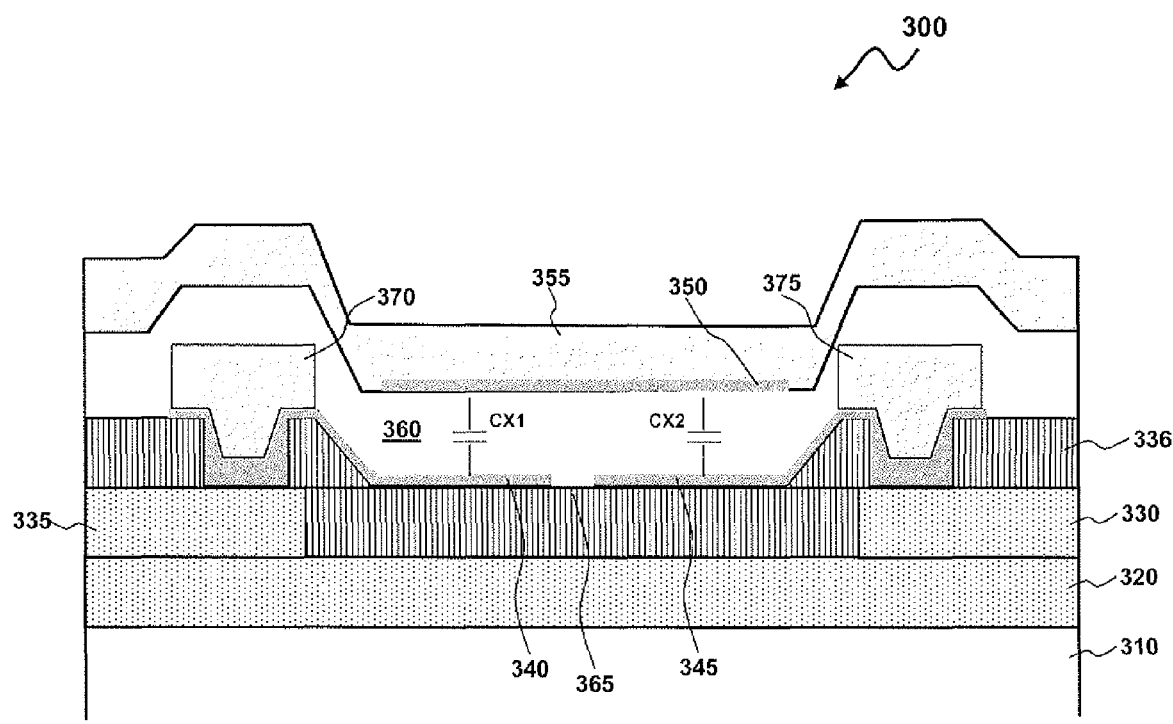
FIG. 3 illustrates a cut-away side view of a relative humidity sensor, in accordance with a preferred embodiment.

Referring to FIG. 3, a cut-away side view of a relative humidity sensor 300 is illustrated, in accordance with a preferred embodiment. The humidity sensor 300 depicted in FIG. 3 can be used for humidity control in, for example, an air conditioner or to detect humidity for weather observation purposes. It is understood, however, that a wide variety of other applications for humidity sensor 300 can also be implemented, depending upon design goals and considerations. As depicted in FIG. 3, an N-type silicon substrate 310 can be employed whereon a silicon oxide film 320 can be formed on the semiconductor substrate 310 as a first insulation film. First and second electrodes 330 and 335 are configured on an identical plane of the silicon oxide film 320 so as to oppose each other with a gap 365 interposed between them.

A material capable of being utilized in a normal semiconductor producing line can be employed to form the first and second electrodes 330 and 335. Such material can be, for example Al, Ti, Au, Cu, poly-Si, and the like. In one particular embodiment, a silicon nitride film 336 can be formed on the electrodes 330 and 335 as a second insulation film. It can be appreciated, however, that in other embodiments, materials other than silicon nitride may be utilized to implement film 336. The silicon nitride film 336 can be utilized as a protection film to cover the pair of electrodes 330 and 335. The silicon nitride film 336 can be formed by plasma CVD method or the like, so as to have the same thickness over the whole area on the semiconductor substrate 310.

As shown in FIG. 3, the pair of electrodes 330 and 335 can be equipped with a first electrical contact 370 and a second electrical contact 375 through which the electrodes 330 and 335 are connected to a signal processing circuit (not shown in FIG. 3) for detecting the variation of the electrostatic capacitance between the pair of electrodes 330 and 335, respectively. The electrical contacts 370 and 375 are required to be exposed so that they are connected to the signal processing circuit, and thus are not covered by the silicon nitride film 336. Furthermore, according to such an embodiment, the capacitance type humidity sensor 300 can be formed on the semiconductor substrate 310, and thus the signal processing circuit for detecting the variation of the capacitance type humidity sensor 300 can be formed on the principal surface of the semiconductor substrate 310.

A sensing medium 360 having a permittivity that changes according to humidity can be formed over the silicon nitride film 320 so as to cover the electrodes 330 and 335. A porous platinum top plate 350 having moisture-permeability through which moisture (e.g., water) is allowed to permeate can be formed so as to cover the humidity sensing medium 360. The top plate 350 possesses a higher dielectric constant than that of the sensing medium 360. When water infiltrates into the humidity sensing medium 360, the dielectric constant of the humidity sensing medium 360 is varied in accordance with the amount of water, thereby infiltrating because the dielectric constant of water is large.

As a result, the electrostatic capacitance of the capacitor as indicated by Cx1 and Cx2 constructed by the pair of electrodes 330 and 335 with the humidity sensing medium 360 as a part of the dielectric material. Humidity can be detected on the basis of the electrostatic capacitance between the pair of electrodes 330 and 335, because the amount of water contained in the humidity sensing medium 360 corresponds to the ambient humidity around the capacitance type humidity sensor 300.

As described above, the variation of the electrostatic capacitance between the pair of electrodes 330 and 335 in accordance with the humidity variation of the humidity sensing medium 360 can be increased by forming the top plate 350 having a higher dielectric constant than the sensing medium 360 on the sensing medium 360. Furthermore, as the dielectric constant of the moisture-affected top plate 350 is higher, the variation of the electrostatic capacitance between the pair of electrodes 330 and 335 in accordance with the humidity variation is increased.

The relative humidity sensing capacitor Cx1 and Cx2 can be fabricated utilizing standard silicon wafer processing techniques commonly used to configure existing relative humidity sensors. An area where the moisture-sensitive film 360 can be located on the semiconductor substrate 310 constitutes a humidity-sensing portion 360. Namely, ambient humidity can be detected via the humidity-sensing portion 360 based on the capacitance formed between the detection electrodes 330 and 335 and the capacitive path to the sensing capacitor Cx1 that varies according to a change in humidity around the sensor 300.

Figure 4:
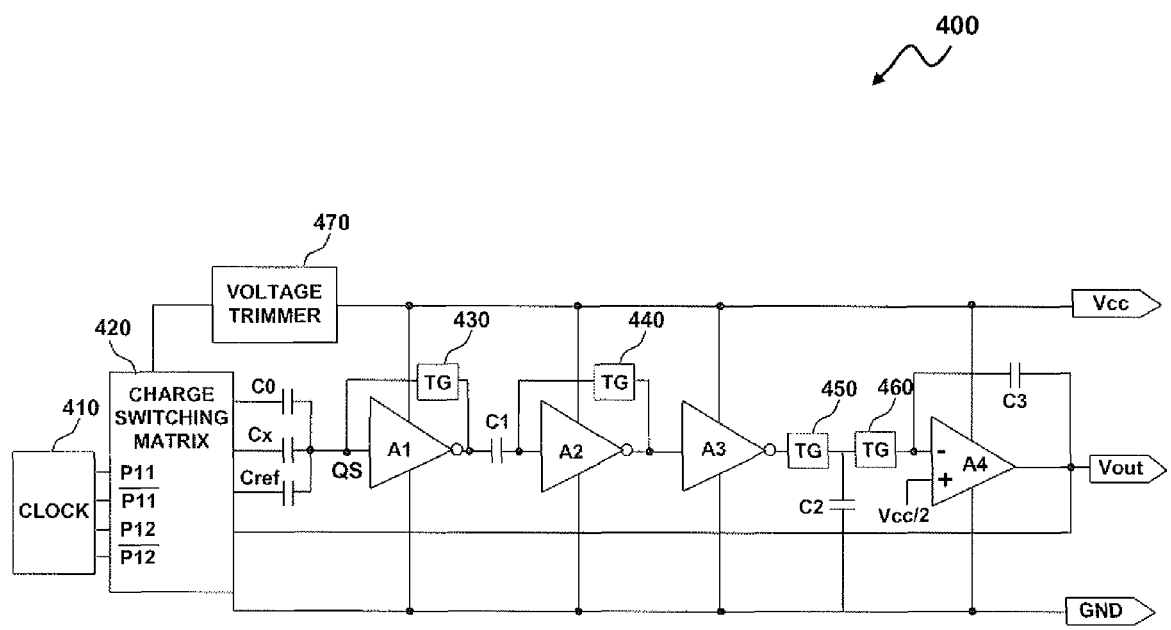
FIG. 4 illustrates an improved charge balancing circuit for transducing relative humidity to a linear voltage, in accordance with a preferred embodiment.

Referring to FIG. 4 illustrated is an improved charge balancing circuit 400 for transducing relative humidity to a linear voltage, in accordance with a preferred embodiment. The charge balancing circuit 400 can be utilized to transduce relative humidity to a linear voltage. The high impedance capacitive nature of the relative humidity sensor 300 can be more readily handled by control of charge. FIG. 4 shows the essential components that include the relative humidity-to-voltage transfer function in terms of a circuit diagram 400. The capacitors C0, C1, C2, C3, and Cref can be designed to be insensitive to humidity and can be fabricated at the same time and from the same materials. Thus, while their absolute values of capacitance will vary, the ratios can be tracked very closely. The relative humidity sensing capacitor Cx can be designed to be sensitive to humidity and can be fabricated at a different time and from different materials than the fixed capacitors C0, C1, C2, C3, and Cref.

A charge switching matrix 420 can be utilized to vary the wiring scheme for capacitors: Cx, C0, and Cref utilizing two-phase, non-overlapping, dual polarity clocks, as can be provided by clock generator 410. Note that one end of all three capacitors Cx, C0, and Cref can be always connected in common, thus providing a charge summing node Qs. Inverters A1, A2, and A3, and capacitor C1, and the pair of associated transmission gates 430 and 440 form a high gain comparator. C2 and its pair of associated transmission gates 450 and 460 illustrates a switched capacitor equivalent of a resistor which can be coupled with amplifier A4 and feedback capacitor C3 in order to form an integrator. The circuit 400 can include an adjustable voltage trimmer 470 for modification of the supply voltage Vcc to VCx for the sensing capacitor Cx and VC0 for the fixed capacitor C0.

Figure 5A:
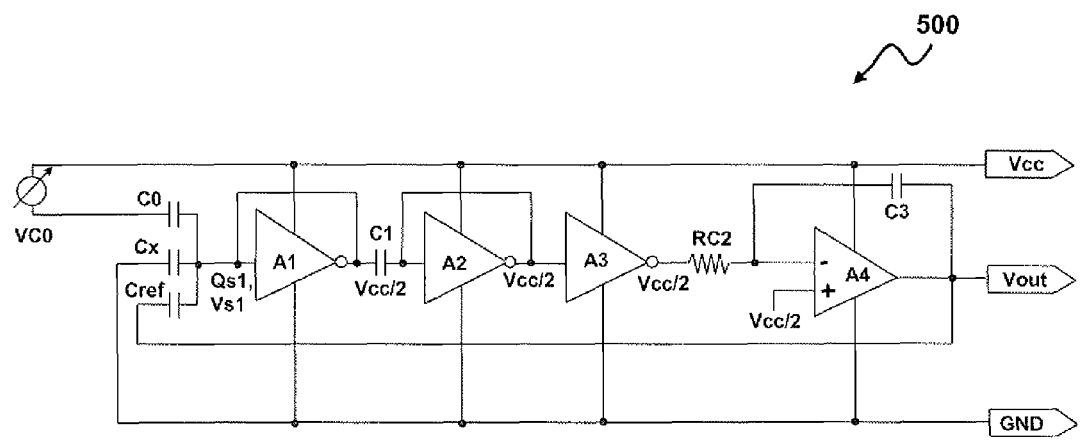
FIG. 5A illustrates the improved charge balancing circuit during a Phase 1 operation, in accordance with a preferred embodiment.
Figure 5B:
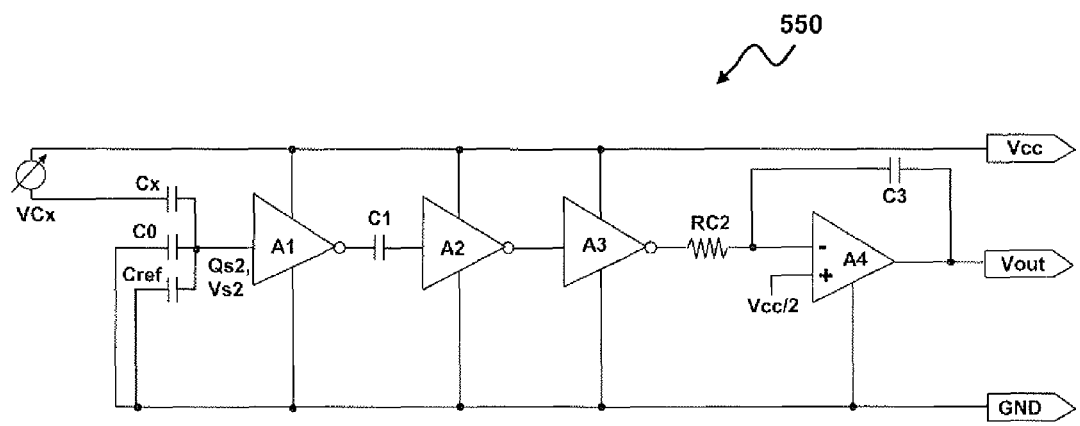
FIG. 5B illustrates the improved charge balancing circuit during a Phase 2 operation, in accordance with a preferred embodiment.

FIGS. 5A and 5B illustrate the circuit connectivity 500 and 550 of the improved charge balancing circuit 400 during "Phase 1" and "Phase 2" respectively. Neglecting Cref for the moment and concentrating on C0 and Cx, note that they effectively form a voltage divider. The charge in the sensing capacitor Cx and the fixed capacitor C0 can be controlled separately by adjusting and/or trimming the supply voltage Vcc utilizing a voltage trimmer 470 in order to achieve capacitive balance. The slope and offset of the relative humidity sensor 300 can also be modified and controlled to particular desired values by adjusting the voltage for the sensing capacitor Cx and the fixed capacitor C0 respectively.

Hence, in Phase 1 C0 can be pulled up to VC0 by adjusting or trimming the supply voltage Vcc utilizing a voltage trimmer 470 and Cx can be pulled down to GND. Similarly, in Phase 2 Cx can be pulled up to VCx and C0 can be pulled down to GND. Thus a periodic differential voltage can be created which is a function of difference in capacitance values. Those skilled in the art will recognize this as a half bridge sensor configuration. During Phase 1, the inverters A1 and A2 short the input node to the output node, which, when implemented with complementary FETs, forms a voltage divider.

FIG. 5A indicates that the three inverters A1, A2 and A3 can be designed to produce a half supply transfer function in this configuration, thus driving both the charge summing node and the output of A3 to Vcc/2 during Phase 1. During Phase 2 these transmission gate shorts can be opened up in order to create a high gain inverting comparator, which allows small movement in the charge summing node voltage relative to Vcc/2 to drive the output of A3 to Vcc or GND. Thus A3, the output of the comparator, controls the integrator. During Phase 1, the output of A3 and the non-inverting input of A4 are both at Vcc/2, which puts the integrator into a "Hold" state. So Phase 1 can be considered as a measurement or sampling phase during which Cref can be charged.

During Phase 2 Cref can be disconnected from the integrator output and reconnected to GND and the comparator responds to the charge-summing node. If the comparator output goes to GND, then the output of the integrator increases linearly. If the comparator output goes to Vcc, then the output of the integrator decreases linearly. If the charge-summing node effectively remains at Vcc/2 during Phase 2, then the integrator remains in the "Hold" state. So Phase 2 can be thought of as the negative feedback adjustment phase. The following equations mathematically describe the operation of the circuit 500 and 550. Equations (1) and (2) calculate the charge at the summing node during Phase 1 and 2, respectively. The negative feedback results in Qs1 and Vs1 being substantially equal to Qs2 and Vs2. Equation (3) mathematically describes the resulting transfer function for the complete circuit operation.

$$Qs1 = Cx*Vs1 + C0*(Vs1-VC0) + Cref*(Vs1-Vout) \quad (1)$$

$$Qs2 = Cx*(Vs2-VCx) + C0*Vs2 + Cref*Vs2 \quad (2)$$

$$Vout = VCx*(Cx/Cref) - VC0*(C0/Cref) \quad (3)$$

As described and shown with respect to FIG. 3, the adjustments made to Cx can be divided substantially equally between Cx1 and Cx2 to minimize the sensitivity reduction due to mismatch error. The supply voltage Vcc can be trimmed or adjustable to VCx for RH (Relative Humidity) sensitive capacitor Cx and/or VC0 for fixed Capacitor C0 in order to control the charge in the capacitors Cx and C0. Hence, the offset i.e., the output value at 0RH, and the sensitivity over entire RH. Span of the Relative humidity sensor circuit 400 can be modified and controlled to particular desired values. The ability of adjusting the charge level both in Cx and C0 provides for better control of the sensor output accuracy. Also by replacing the trimming site from the exposed Cx to a network in the circuit the reliability of the sensor can be enhanced considerably.

Figure 6:
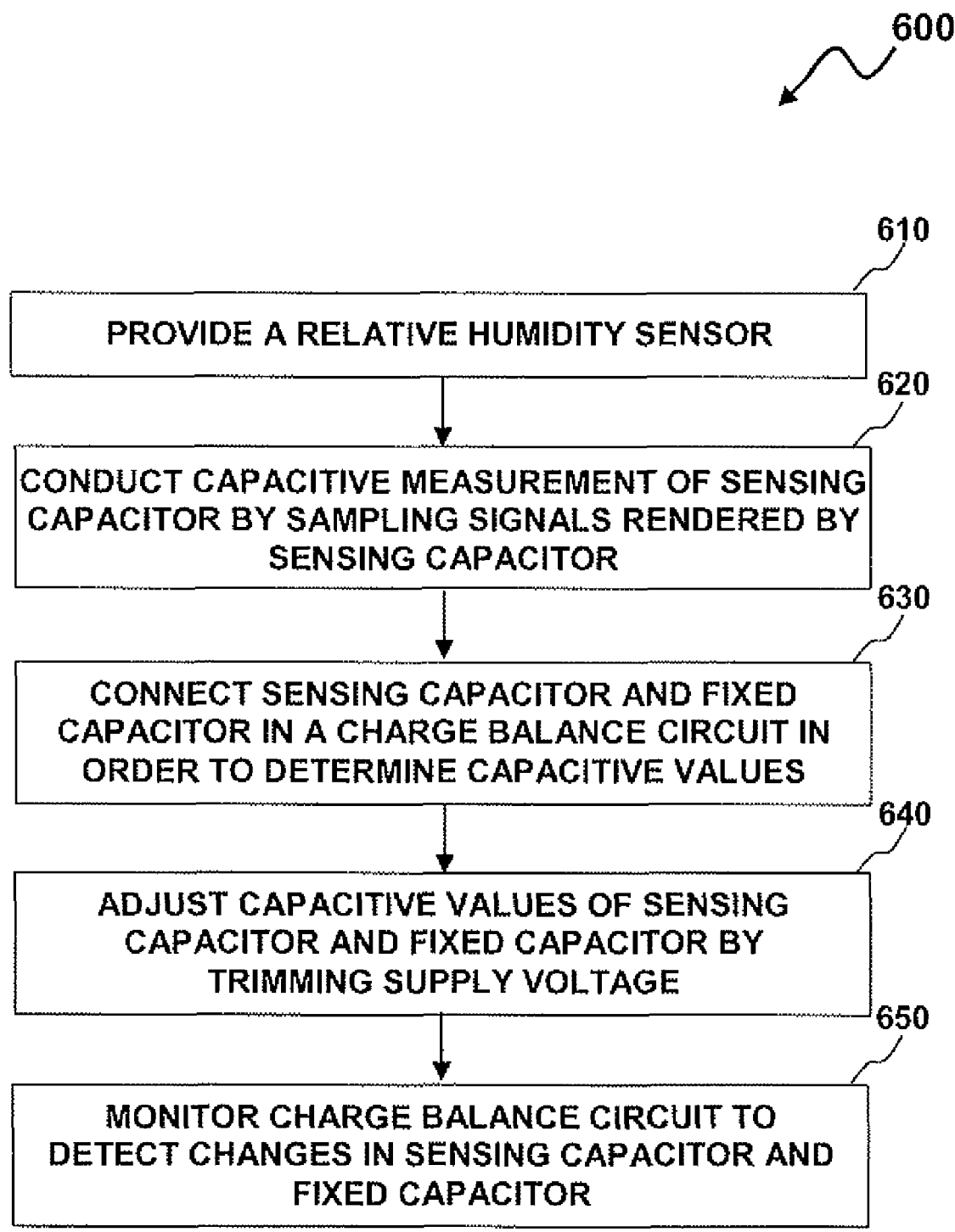
FIG. 6 illustrates a high-level logical flowchart of operations illustrating logical operational steps of a method for adjusting characteristics of the relative humidity sensor, in accordance with a preferred embodiment.

Referring to FIG. 6, a high-level logical flowchart of operations illustrating logical operational steps of a method 600 for adjusting characteristics of the relative humidity sensor 300 is illustrated, in accordance with a preferred embodiment. A relative humidity sensor such as a sensor 300 as depicted in FIG. 3 can be provided, as illustrated at block 610. Thereafter, as indicated at block 620, capacitive measurement of sensing capacitor Cx can be conducted by sampling signals rendered by the sensing capacitor Cx.

The sensing capacitor Cx and a fixed capacitor C0 can be connected in a charge balance circuit in order to determine capacitive values, as shown at block 630. Next, as described at block 640, the capacitive values of sensing capacitor Cx and fixed capacitor C0 can be adjusted by trimming supply voltage Vcc to VCx and VC0 respectively. The charge balance circuit can be monitored to detect changes in sensing capacitor Cx and fixed capacitor C0, as depicted at block 650. The resulting transfer function for the complete circuit operation is described in equations (7) and (8).

$$Vout = VCx*[Cx*(1+\alpha*RH)/Cref] - VC0*(C0/Cref) \quad (7)$$

$$Vout = (VCx/Cref)*[Cx*(1+\alpha*RH)] - VC0*(C0/Cref), \quad (8)$$

where 'α' represents the property of polyimide coefficient and RH represents relative humidity. The present device is used to sense the relative humidity in the ambient environment around the sensor. During operation, a relative humidity level is sensed and then the sensor 300 generates a voltage output proportional to the relative humidity. This voltage can then be used by other circuits to implement functions such as relative humidity control, enthalpy control for building HVAC, weather sensing instruments, process controls for drying, process controls for batch or continuous production where relative humidity is a parameter that controls the output of a process or is related to some process variable to be controlled, length or end of cycle in drying applications, and other applications.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A relative humidity sensor, comprising:
    a pair of electrodes having a gap formed there between and including within the gap a humidity sensitive film, said pair of electrodes, said film and said gap forming a sensing capacitor wherein changes in humidity affect said humidity sensitive film and thereby changes the capacitive value of said sensing capacitor;
    a fixed capacitor connecting said sensing capacitor in a charge balance circuit, said charge balance circuit used to determine capacitive values of said sensing capacitor; and
    a supply voltage adapted to separately control charge in said sensing capacitor and said fixed capacitor, wherein control of said supply voltage enables modification and control over slope and offset of said relative humidity sensor.

2. The relative humidity sensor of claim 1 further comprising a monitor adapted to monitor said charge balance circuit to detect changes in said sensing capacitor.

3. The relative humidity sensor of claim 2 wherein said supply voltage is adapted to be trimmed in order to separately control charge of said sensing capacitor and said fixed capacitor until desired values of offset and slope are achieved.

4. The relative humidity sensor of claim 2 wherein said supply voltage further comprises a voltage trimmer adapted to modify supply voltage.

5. The relative humidity sensor of claim 1 wherein said supply voltage is adapted to be trimmed in order to separately control charge of said sensing capacitor and said fixed capacitor until desired values of offset and slope are achieved.

6. The relative humidity sensor of claim 5 further comprising a monitor adapted to monitor said charge balance circuit to detect changes in said sensing capacitor.

7. The relative humidity sensor of claim 1 wherein said supply voltage further comprises of a voltage trimmer adapted to modify supply voltage.

* * * * *